United States Patent [19]
Andrade

[11] Patent Number: 5,855,202
[45] Date of Patent: Jan. 5, 1999

[54] AEROSOL HOLDING CHAMBER FOR A METERED-DOSE INHALER

[76] Inventor: Joseph R. Andrade, 131 Fox Meadow Rd., Scarsdale, N.Y. 10583

[21] Appl. No.: 946,985

[22] Filed: Oct. 8, 1997

[51] Int. Cl.⁶ .................................................. A61M 11/00
[52] U.S. Cl. ............................... 128/200.14; 128/200.23; 128/203.12; 128/206.29
[58] Field of Search .................... 128/200.14, 200.22, 128/200.23, 203.12, 206.29, 203.23

[56] References Cited

U.S. PATENT DOCUMENTS

| | | | |
|---|---|---|---|
| 4,470,412 | 9/1984 | Nowacki et al. | 128/200.23 |
| 5,012,803 | 5/1991 | Foley et al. | 128/200.23 |
| 5,297,543 | 3/1994 | Larson et al. | 128/203.23 |
| 5,571,246 | 11/1996 | Alldredge | 128/200.23 |
| 5,598,836 | 2/1997 | Larson et al. | 128/200.23 |

*Primary Examiner*—Aaron J. Lewis
*Attorney, Agent, or Firm*—Herbert Dubno; Andrew Wilford

[57] ABSTRACT

A metered-dose inhaler having a medication-containing cartridge and a tubular outlet is used with an aerosol holding chamber having an elongated body having a rear end wall formed with a hole shaped to fit snugly around the tubular outlet of the inhaler, a longitudinally extending side wall, and a front end wall. A mouthpiece formed on the front end wall has a large-diameter tubular rear portion extending forward from the front end wall, a small-diameter tubular front bite portion extending forward from the large-diameter rear portion, and a transverse wall between the rear and front portions and extending generally perpendicular thereto. The front bite portion is of a height equal to at most half a height of the large-diameter rear portion.

6 Claims, 1 Drawing Sheet

AEROSOL HOLDING CHAMBER FOR A METERED-DOSE INHALER

FIELD OF THE INVENTION

The present invention relates to an aerosol holding chamber for a metered-dose inhaler.

BACKGROUND OF THE INVENTION

A standard metered-dose inhaler, such as sold under the trade name "Flovent" by GlaxoWellcome, "Proventil" or "Vanceril" by Key Pharmaceutical, or "Aerobid" by Forest Pharmaceuticals, comprises a small pressurized medication-filled cartridge and a holder formed with a short tubular mouthpiece. After shaking the device the mouthpiece is inserted into the mouth between the lips and teeth. Then as the patient takes a slow deep breath the cartridge is depressed to release a puff of the medication that is then drawn down into the lungs, normally to apply an anti-inflammatory agent to them.

Such a system is extremely effective only if used perfectly. That is the puff of medication must be blown into the oral cavity while the patient is inhaling so that it will travel to the lungs. The problem is that it is invariably being used by those suffering from breathing difficulties who are in fact often gasping for breath when the device is being used so that getting the procedure correct is a problem, in particular for children.

This has lead to the development of aids that are used with an inhaler. One such as described in U.S. Pat. No. 5,012,804 has a rigid cylindrical chamber provided at one end with a tubular extension serving as mouthpiece and of substantially the same size and shape as the mouthpiece of the inhaler. The other end of the chamber is provided with a hole into which the mouthpiece of the inhaler is fitted and a one-way valve at this other end allows air to be drawn into the chamber. Thus, after fitting the inhaler to the chamber, the user places the mouthpiece of the holding chamber in his mouth, actuates the inhaler to shoot a puff of the medication into the chamber, and then slowly inhales to draw in the charge from the chamber. Such an arrangement can even allow the user to draw in the medication in two breaths.

Another such system sold under the trade name "InspirEase" by Schering Pharmaceutical has a collapsible chamber and the inhaler cartridge is fitted to the mouthpiece between the chamber and the outer end that is inserted into the patient's mouth. With this system the chamber is expanded and the medication is blown into it, then the user breathes in the air from the chamber until same is completely collapsed. Once again this system allows the dose to be consumed in two breaths.

The disadvantage of these known systems is that they still require the patient to use them very, very carefully. The medication must be drawn straight into the oral cavity so that it then passes down into the lungs. If, for instance, the mouthpiece is only gripped between the lips, it is possible for the incoming stream of air to impinge on the front teeth so that much of the medication will simply be applied as a film to the teeth where it is does no good. These administration problems are particularly great with children who often cannot master the procedure for properly taking in the needed drug.

OBJECTS OF THE INVENTION

It is therefore an object of the present invention to provide an improved aerosol chamber for a metered-dose inhaler.

Another object is the provision of such an improved aerosol chamber for a metered-dose inhaler which overcomes the above-given disadvantages, that is which is simple to use, even for a child, and which insures proper administration of the dose from the inhaler.

SUMMARY OF THE INVENTION

A metered-dose inhaler having a medication-containing cartridge and a tubular outlet is used with an aerosol holding chamber having according to the invention an elongated body having a rear end wall formed with a hole shaped to fit snugly around the tubular outlet of the inhaler, a longitudinally extending side wall, and a front end wall. A mouthpiece formed on the front end wall has a large-diameter tubular rear portion extending forward from the front end wall, a small-diameter tubular front bite portion extending forward from the large-diameter rear portion, and a transverse wall between the rear and front portions and extending generally perpendicular thereto. The front bite portion is of a height equal to at most half a height of the large-diameter rear portion.

Thus with this system the front bite portion is gripped between the teeth while the lips are pressed against the transverse wall. This ensures that the medication in the chamber will be directed past the teeth and lips directly into the oral cavity, not simply against the teeth as is common when such an inhaler is used carelessly. The end wall prevents leakage around the bite tube. The result is effective administration of the inhaler's medication, even for a child who does not use the device carefully.

The height of the front portion is in accordance with the invention at most a third the height of the rear portion. In addition according to the invention the side wall has a front region that tapers toward the front end wall so as to direct the flow from inside the chamber through the mouthpiece. Furthermore in accordance with the invention the mouthpiece is formed with a pair of generally coplanar flat wings generally centered on the front and rear portions. These wings force the user to properly orient the device with respect to the vertical, as the inhaler must be used upright to which end its outlet as well as the hole in the rear end wall are both horizontally elongated.

The height of the front portion is according to the invention at most about 1 cm and the height of the rear portion is at least about 2 cm. Furthermore the portions are tubular and coaxial and the front bite portion has a length of at least about 1 cm.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
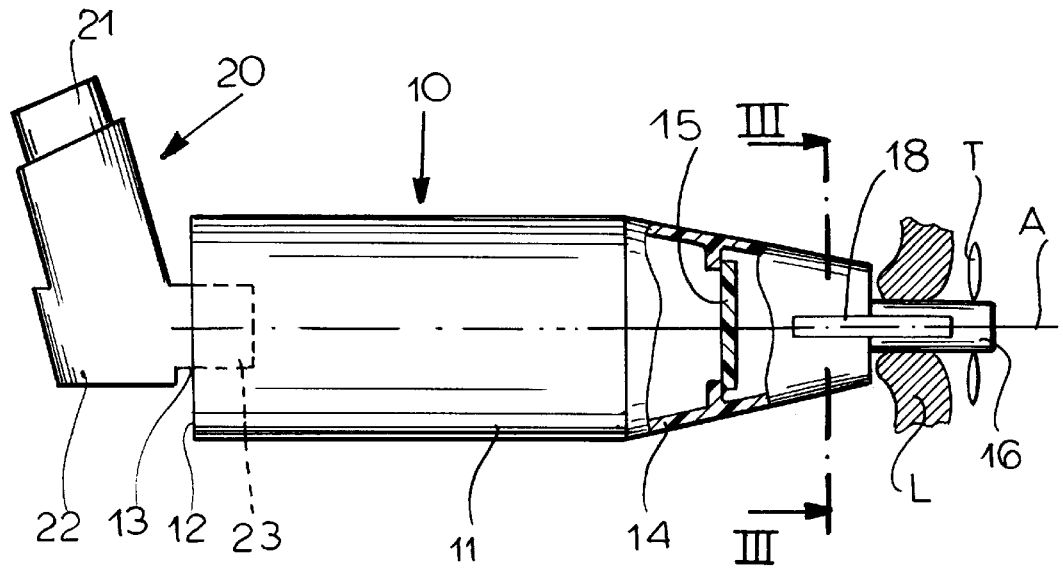
FIG. 1 is a side partly diagrammatic and partly sectional view illustrating the system of this invention.
Figure 2:
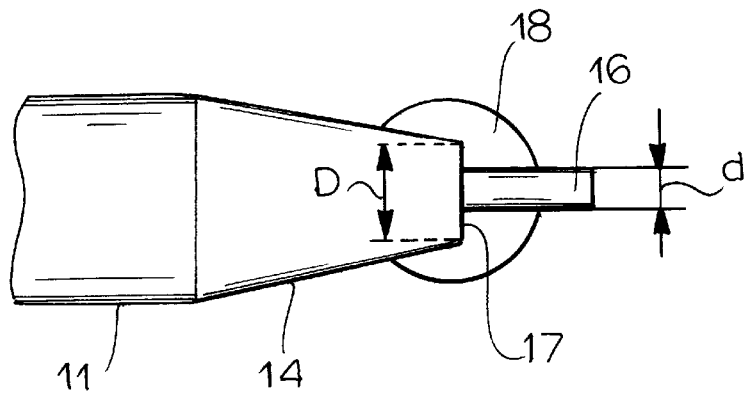
FIG. 2 is a top view of a front portion of the chamber according to the invention.
Figure 3:
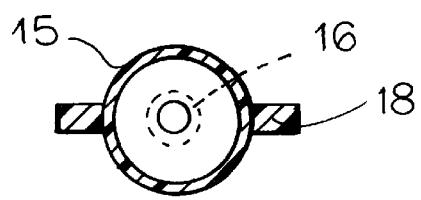
FIG. 3 is a cross section taken along line III—III of FIG. 1.

As seen in FIGS. 1 through 3 the system of this invention comprises an aerosol holding chamber 10 adapted to be used with a standard metered-dose inhaler 20. The inhaler 20 has a standard pressurized cartridge 21, a body 22, and a mouthpiece or outlet 23 projecting laterally from the body 22. This inhaler 20 is suitable for stand-alone use for a patient who can be guaranteed to follow precise drug-administration instructions with each use.

The chamber 10 has a tubular and cylindrical body 11 centered on an axis A and provided with a perpendicular rear end wall 12 formed with a horizontally elongated central hole 12 adapted to fit complementarily around the mouthpiece 23. Its opposite front end is formed with a frustoconically tapered wall 14 from which coaxially extends a small-diameter tubular portion 16. The tapering side wall 14 has a planar end wall 17 from which the tube 16 extends. A pair of bite wings 18 are formed on the front end, lying in a plane including the axis A and extending diametrally to both sides of the portions 15 and 16 with part-circular outer edges. Internally a flap 15 acting as a check valve extends crosswise across the side wall 14.

The entire chamber 10 is molded of one piece of a fairly rigid plastic like polyethylene. The small-diameter front portion or tube 16 has a diameter or height d equal to about one third of a diameter or height D of a small-diameter end of the wall 14. Thus in use the front portion 16 is gripped between the teeth T and lips L of the user, with the lips L pressed against the wall 17 so that this wall 17 effectively closes the mouth around the tube 16. The length L of this tube 16, here around 1.5 cm, is sufficient that when the wall 17 is pressed against the outer surface of the lips L, the tube 16 will project past the teeth T well into the oral cavity. Thus when the inhaler 20 is actuated, it emits a puff of its medication into the chamber 10 from which it can be drawn easily by the patient, with the medication being directed past the lips L and teeth T into the oral cavity, whence it can travel to the lungs. The check-valve flap 15 prevents air from being blown back into the chamber 10.

The bite wings 18 are useful to ensure that the inhaler 20 is held in the desired upright position as the complementary hole 13 and mouthpiece 23 are of horizontally elongated shape so they only fit together in a position with the inhaler 20 perpendicular to the bite wings 18. The device is therefore going to be used correctly even by a child.

I claim:

1. In combination with a metered-dose inhaler having a medication-containing cartridge and a tubular outlet, an aerosol holding chamber comprising:

an elongated body having a rear end wall formed with a hole shaped to fit snugly around the tubular outlet of the inhaler, a longitudinally extending side wall, and a front end; and a mouthpiece formed on the front end and having
      a large-diameter tubular rear portion extending forward from the front end,
      a small-diameter tubular front bite portion extending forward from the large-diameter rear portion, and
      a transverse wall between the rear and front portions and extending generally perpendicular thereto, the front bite portion being of a height equal to at most one-third a height of the large-diameter rear portion.

2. The aerosol holding chamber defined in claim 1 wherein the height of the front portion is at most about 1 cm and the height of the rear portion is at least about 2 cm.

3. The aerosol holding chamber defined in claim 1 wherein the portions are tubular, and coaxial.

4. The aerosol holding chamber defined in claim 1 wherein the front bite portion has a length of at least about 1 cm.

5. In combination with a metered-dose inhaler having a medication-containing cartridge and a tubular outlet, an aerosol holding chamber comprising:

an elongated body having a rear end wall formed with a hole shaped to fit snugly around the tubular outlet of the inhaler, a longitudinally extending side wall, and a front end; and a mouthpiece formed on the front end and having
      a large-diameter tubular rear portion extending forward from the front end,
      a small-diameter tubular front bite portion extending forward from the large-diameter rear portion,
      a transverse wall between the rear and front portions and extending generally perpendicular thereto, the front bite portion being of a height equal to at most half a height of the large-diameter rear portion, and
      a pair of generally coplanar flat wings generally centered on the front and rear portions.

6. In combination with a metered-dose inhaler having a medication-containing cartridge and a tubular outlet, an aerosol holding chamber comprising:

an elongated generally cylindrical body having a transverse rear end wall formed with a hole shaped to fit snugly around the tubular outlet of the inhaler, a longitudinally extending side wall centered on an axis and having an axially forwardly tapering front end region having a front end; and a mouthpiece projecting from the front end and having
      a large-diameter tapering tubular rear portion extending forward from the front end,
      a small-diameter cylindrically tubular front bite portion extending forward from the large-diameter rear portion,
      a transverse wall between the rear and front portions and extending generally perpendicular to the axis, the front bite portion being of a height equal to at most half a height of the large-diameter rear portion, and
      a pair of generally coplanar flat wings generally centered on the front and rear portions and projecting diametrally oppositely therefrom.

* * * * *